United States Patent [19]
Lynch

[11] 3,986,213
[45] Oct. 19, 1976

[54] GEL FILLED MEDICAL DEVICES

[75] Inventor: Henry Wilfred Lynch, Racine, Wis.

[73] Assignee: Medical Engineering Corporation, Racine, Wis.

[22] Filed: May 27, 1975

[21] Appl. No.: 580,977

[52] U.S. Cl. ............................................. 3/36; 3/20; 128/83; 128/DIG. 21; 5/367; 5/370
[51] Int. Cl.² ...................... A61F 1/24; A41C 3/10
[58] Field of Search ............................... 3/36, 1, 20; 128/DIG. 21, 462, 83, 478–481; 2/267; 5/365, 367, 368, 370

[56] References Cited
UNITED STATES PATENTS

| 2,542,619 | 2/1951 | Bernhardt | 3/36 |
| 3,308,491 | 3/1967 | Spence | 5/367 |
| 3,494,365 | 2/1970 | Beals | 3/36 X |
| 3,548,420 | 12/1970 | Spence | 5/367 |
| 3,896,506 | 7/1975 | Hankin et al. | 3/36 |

FOREIGN PATENTS OR APPLICATIONS

| 1,110,479 | 4/1968 | United Kingdom | 3/36 |

Primary Examiner—Ronald L. Frinks
Attorney, Agent, or Firm—Andrus, Sceales, Starke & Sawall

[57] ABSTRACT

A mammary prosthesis or orthopedic pad includes a flexible shell formed of silicone rubber. The shell is filled with a silicone gel, the specific gravity of which is reduced by a dispersion of glass or epoxy microspheres.

7 Claims, 3 Drawing Figures

GEL FILLED MEDICAL DEVICES

BACKGROUND OF THE INVENTION

Mammary prostheses which comprise flexible shells of a silicone polymer filled with a silicone gel are disclosed in U.S. Pat. No. 3,293,663 and U.S. Pat. No. 3,665,520. Silicone gel is generally considered to be an ideal material for surgical implants as it has a natural tissue like resiliency it does not cause tissue reaction, and it has approximately the same specific weight as normal mammary tissue. However, recently it has been determined that in some instances the fact that silicone gel has a specific weight approximately the same as normal human mammary tissue is not an advantage and that a lighter material might be more suitable. In an implanted mammary prosthesis of significant size a lighter weight material is preferred because the weight of a mammary prosthesis is carried to a large extent solely by the skin capsule in which it is implanted whereas, the weight of normal mammary tissue is distributed fairly evenly through its attachment to the fascia and via the supporting Cooper's ligaments. A lighter material is often desirable in an external mammary prosthesis because the entire weight of such a prosthesis is concentrated on the shoulder straps of the brassiere. Previous attempts to develope a lighter weight silicone gel have been unsuccessful as they have resulted in prostheses which either lacked the resiliency of normal tissue or else contained materials that were palpable.

SUMMARY OF THE INVENTION

It has now been discovered that a prosthesis of more desirable weight may be prepared by filling a flexible shell with a silicone gel in which there has been incorporated hollow microspheres of glass, ceramic or epoxy material. It has also been found that such prosthesis possesses an additional advantage. For example, in addition, to retaining the natural tissue-like resiliency of a conventional silicone gel filled prosthesis the novel prosthesis of the present invention when surgically implanted results in a more natural appearing implant. The superior appearance upon implantation apparently is due to the creamy white color of the novel prosthesis of the present invention. Conventional gel filled prostheses are colorless and if implanted close to the surface of the skin result in the area about the implant appearing discolored or having a bluish cast or tinge as compared to normal tissue.

Other advantages of the present invention will be apparent from the following description which is to be read in conjunction with the drawings in which.

DETAILED DESCRIPTION OF THE INVENTION

Figure 1:
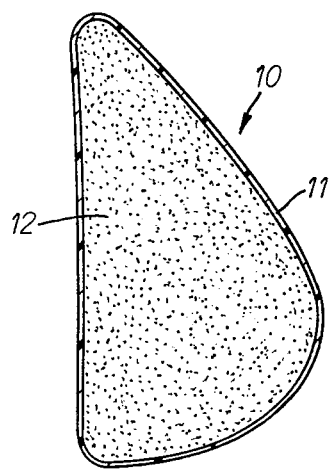
FIG. 1 is a cross-sectional view of a mammary prosthesis incorporating the present invention.

In the drawing, a mammary prosthesis 10 is shown in FIG. 1 and it is seen to comprise a flexible shell 11 filled with a mixture 12 of silicone gel and microspheres. The container or shell 11 is preferably formed of a silicone rubber or elastomer such as MEC 127, which is available from Medical Engineering Corporation of Racine, Wisconsin. If desired, an organosiloxane copolymer of the type set forth in U.S. Pat. No. 3,665,520 may be used. The material of the shell should preferably have low modulus, but high ultimate tensile and tear strengths. In addition, if intended for implant use the shell material should not cause tissue reaction.

Figure 2:
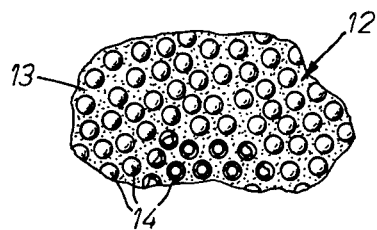
FIG. 2 is an enlarged cross-sectional view of a portion of the prosthesis of FIG. 1.

As seen in FIG. 2, the mixture 12 is comprised of a major portion of silicone gel 13 and a minor portion of hollow microspheres 14 which are completely surrounded by the gel. The silicone gel preferred for use is one having a specific gravity of about 0.89 to 0.95. One such gel is the 2 component RTV system commercially available from the Dow-Corning Company under the numbers X72146 and X72150 or X72167 and X72168. Another suitable gel is that available from General Electric under the numbers RTV 6193A and 6193B or RTV 6195A and 6195B. The hollow microspheres preferred for use in the invention are hollow glass spheres having a diameter of from 44 to 175 microns, a wall thickness of about 2 microns and a bulk density of about 0.194 g/cc. The microspheres available from Emerson and Cuming of Canton, Mass. under the name MICROBALLOONS Grade 16101 (R and FT 102) are preferred. Another type of sphere that can be used is that available commercially under the name ECCOSPHERES EP 100 from Emerson and Cuming of Canton, Mass. They are made of epoxy plastic, have diameters of from 0.070 to 0.150 inches and a bulk density of 0.12 g/cc.

The preparation of a surgical prosthesis of the present invention is readily accomplished by first mixing the desired ratio of microspheres and silicone gel to insure even distribution of the microspheres throughout the gel and to eliminate any air bubbles, then filling the preformed shells with the mixture, sealing the shell, preferably by gluing a patch of the same material as the shell material over the opening through which the mixture was introduced, and finally sterilizing the prosthesis prior to implantation.

Although other ratios of microspheres to silicone gel may be used, a mixture of 15% of the preferred microspheres to 85% of the silicone gel on a weight to weight basis is preferred. Such a mixture has a specific gravity of about 0.75 whereas, the conventional silicone gel used to fill a mammary prosthesis has a specific gravity of about 0.9. The use of the described microsphere and gel mixture in place of the conventional gel results in a weight reduction of about 15%. In addition, the mixture is of a white creamy color, probably due to the refraction of light by the microspheres. Obviously, if only a slight reduction in weight as compared to a conventional silicone gel is desired less of the microsphere need be incorporated and if a greater weight reduction is desired a greater quantity of the microspheres needs to be used. However, there would appear to be little reason to use less than 5% of the microspheres or more than 50% of them by weight.

The use of different gels and microspheres than has been described could result in other ratios being preferred. However, it is important to obtain the maximum benefits that the relationship between the gel and the microspheres be such that the bouyant forces upon the microspheres be less than the adhesive force of the gel so that the microspheres do not separate to form a separate layer at the top of the prosthesis. It is also important that the mixture of microspheres and gel have the resiliency natural tissue and that the microspheres be small enough not to be palpable.

Figure 3:
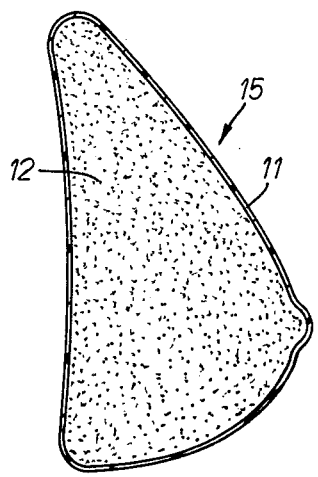
FIG. 3 is a cross-sectional view of an external mammary prosthesis incorporating the present invention.

While the invention has been described primarily in regard to a mammary prosthesis intended for implantation the invention is not that limited. The mixture of microspheres and gel can also be used with advantage in the manufacture of external mammary prostheses such as that shown in FIG. 3 or in other types of prostheses. In addition, the mixture can be used to reduce the weight of orthopedic pads for the prevention and/or treatment of decubitus ulcers.

It will be apparent to those skilled in the art that still other modifications and changes other than those described can be made without departing from the spirit and scope of the present invention.

I claim:

1. A medical device comprising a flexible silicone rubber shell having a filling, said filling comprising a major portion of a silicone gel having uniformly dispersed therein a minor portion of hollow microspheres in a quantity sufficient to reduce the specific gravity thereof to less than that of human tissue, said microspheres having a density substantially less than the silicone gel but being of a size such that the buoyant forces of the microspheres in the gel are less than adhesive forces between the microspheres and the gel, thereby to retain the uniform dispersion of the microspheres.

2. A device of claim 1 in which the mixture of microspheres and gel has the resiliency of natural tissue.

3. A device of claim 1 wherein said hollow microspheres are formed of glass.

4. A device of claim 1 in which the mixture is comprised of 5% to 50% of microspheres and 50% to 95% of gel on a weight to weight basis.

5. A device of claim 1 wherein said device comprises a mammary prosthesis.

6. A device of claim 3 wherein said device comprises a mammary prosthesis.

7. A device of claim 4 wherein said device comprises a mammary prosthesis.

* * * * *